(12) United States Patent  
Bak et al.

(10) Patent No.: US 9,731,114 B2  
(45) Date of Patent: Aug. 15, 2017

(54) MULTICHANNEL BRAIN PROBE

(71) Applicants: Martin J. Bak, Potomac, MD (US); Brian H. Bak, Germantown, MD (US)

(72) Inventors: Martin J. Bak, Potomac, MD (US); Brian H. Bak, Germantown, MD (US)

( * ) Notice: Subject to any disclaimer, the term of this patent is extended or adjusted under 35 U.S.C. 154(b) by 729 days.

(21) Appl. No.: 14/204,088

(22) Filed: Mar. 11, 2014

(65) Prior Publication Data

US 2015/0258330 A1 Sep. 17, 2015

(51) Int. Cl.
*A61B 5/04* (2006.01)
*A61N 1/05* (2006.01)
*A61B 5/0478* (2006.01)
*H01R 43/20* (2006.01)
*H01R 43/01* (2006.01)
*A61B 5/00* (2006.01)

(52) U.S. Cl.
CPC .......... *A61N 1/0534* (2013.01); *A61B 5/0478* (2013.01); *A61B 5/6848* (2013.01); *A61B 5/6868* (2013.01); *A61N 1/0529* (2013.01); *H01R 43/01* (2013.01); *H01R 43/20* (2013.01); *Y10T 29/49176* (2015.01)

(58) Field of Classification Search
CPC . A61B 5/04001; A61B 5/4064; A61B 5/6868; A61B 5/0478; A61N 1/0529
See application file for complete search history.

(56) References Cited

U.S. PATENT DOCUMENTS

2002/0198446 A1* 12/2002 Hill ..................... A61B 5/04001
  600/378
2007/0027384 A1* 2/2007 Brister ............... A61B 5/14532
  600/365

* cited by examiner

*Primary Examiner* — Christian Jang
(74) *Attorney, Agent, or Firm* — Don W. Weber

(57) ABSTRACT

An intraoperative multichannel brain probe is presented. The brain probe has a cylindrical upper stainless steel section attached to a lower cylindrical section. In the lower section, an outer cylindrical tube surrounds a second insulating tube. Electrically recording/stimulating wires are placed between the outer tube and the second tube. Each wire has one end protruding out a hole in the outer tube. The other end of each wire is threaded through the entire probe and electrically connected to a recording or stimulating device through a connector system. A number of insulating tubes and electrodes located inside the second tube may also be part of the brain probe. Each inner electrode, typically two, is insulated from each other and from the second insulating tube by other insulating tubes. The combination of one or more wires and electrodes provides a multi-functional device. The brain probe is capable of providing multichannel stimulation and/or recording of brain functions and up to 128 individual electrode conducting sites.

8 Claims, 13 Drawing Sheets

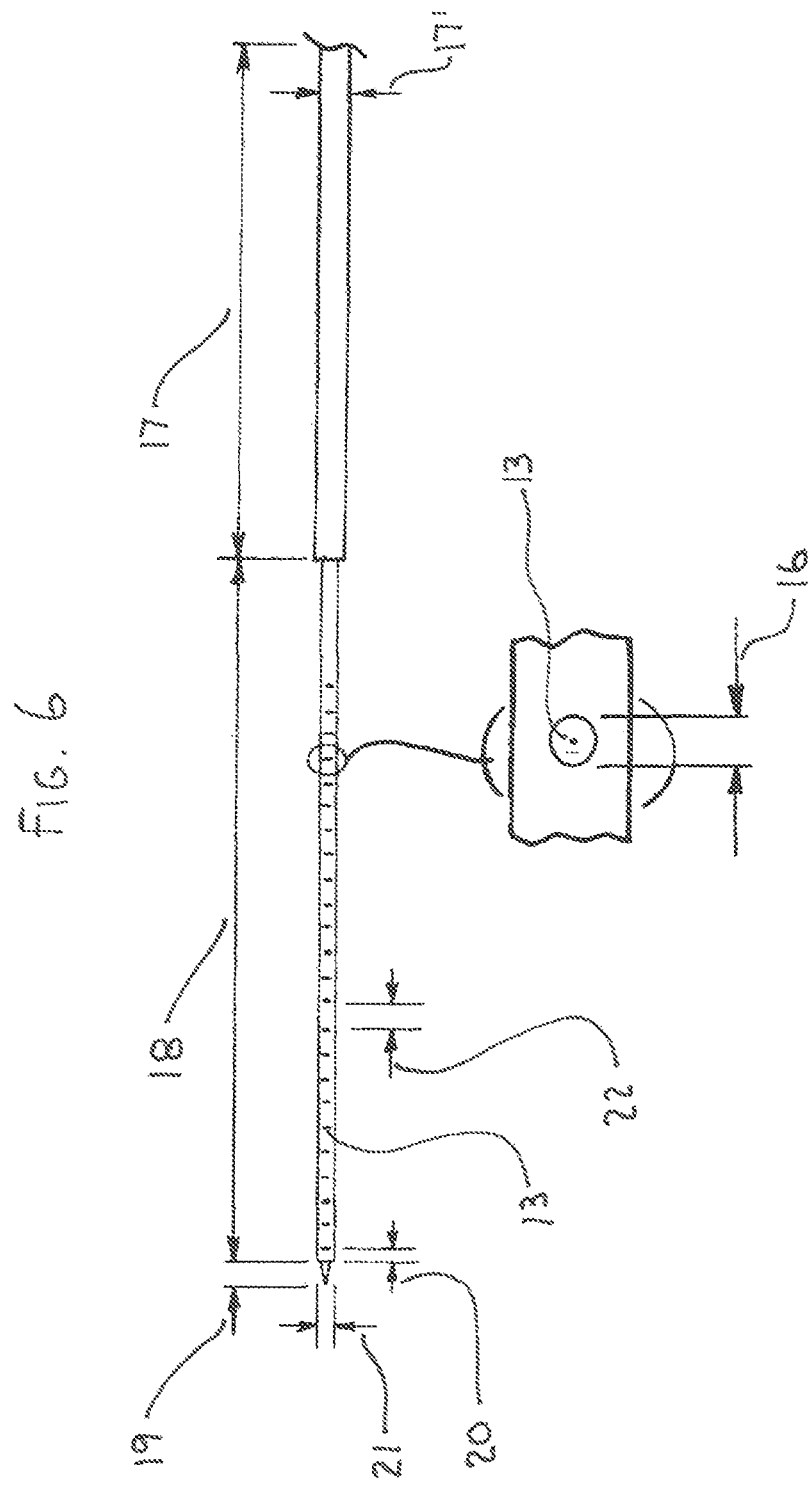

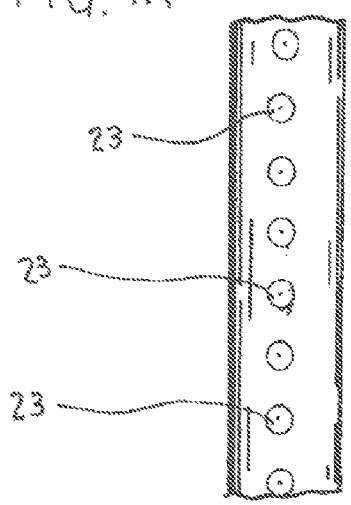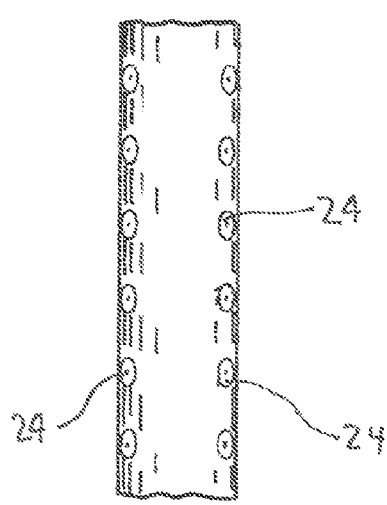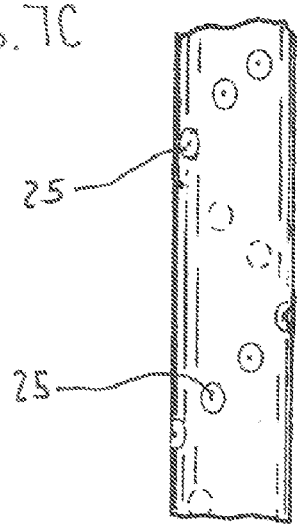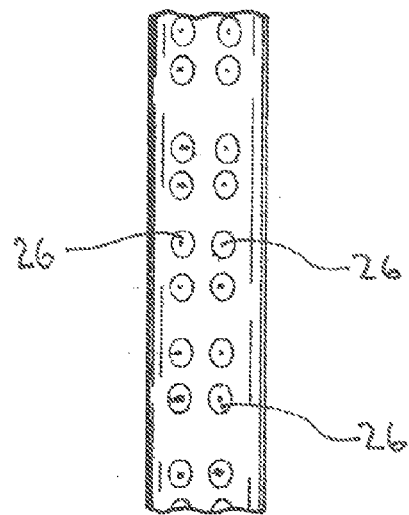

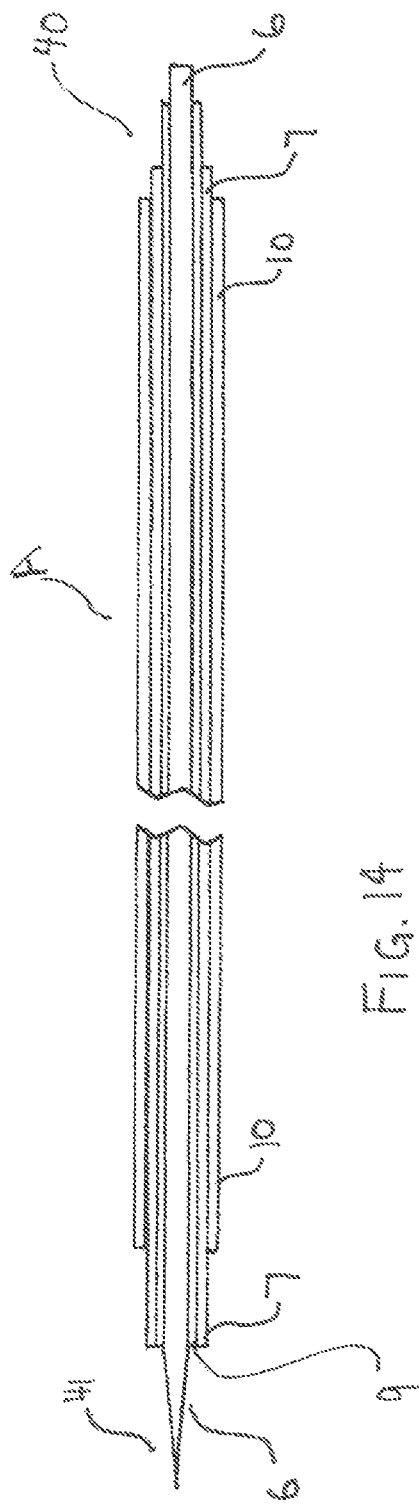

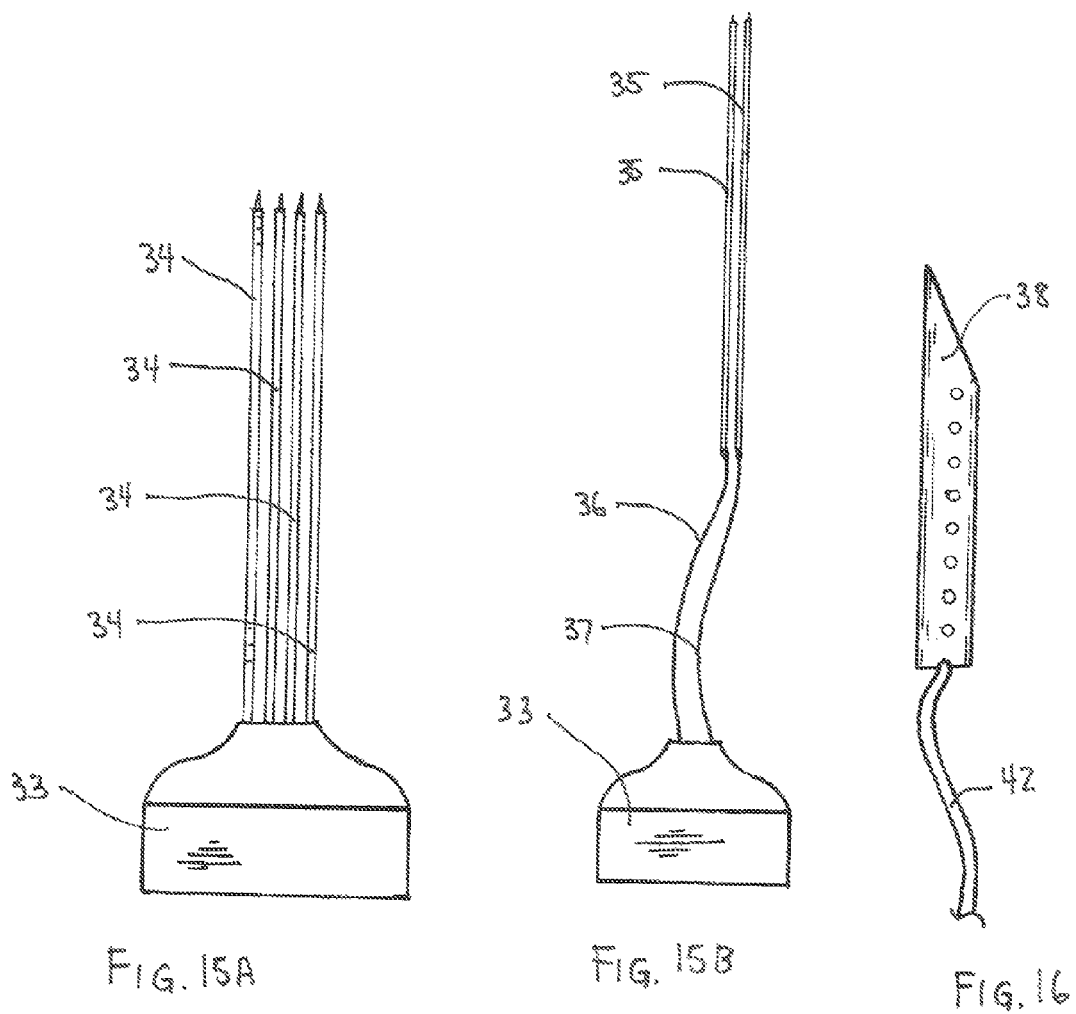

MULTICHANNEL BRAIN PROBE

BACKGROUND OF THE INVENTION

This invention relates to the fields of neuroscience and electrochemistry. A multichannel brain probe for use in animals and humans in particular is presented.

Neurosurgery has made much advancement in the last few years. With the development of micro-electrical devices, it has become possible to insert very small electrode devices into the cranium without damaging the brain matter. These devices are very useful in recording brain functions and in stimulating parts of the brain. The small electrode devices can treat certain neurological problems such as movement disorders, pain and epilepsy. Discrete anatomical sites can be stimulated to have a therapeutic effect. Recording of electrical data can also be used to help diagnose certain conditions.

Deep brain stimulation by a microelectrode has been shown to be useful in combatting Parkinson's disease as one example. However, this approach has a limitation in that only one brain electrode is provided. A single electrode may either stimulate or record, but not both. It is an object of this invention to provide a multichannel brain probe capable of both stimulating and recording in the same device. The probe can also be used as a diagnostic tool for neurosurgeons or as a research tool for neuroscientists.

Determining which area of the brain to stimulate or record is a complex and difficult task. The use of a multichannel brain probe with a number of discreet microrecording and microstimulating sites also aids the surgeon as it allows him to physiologically determine the location of both target and non-target areas deep within the brain. It is highly desirable if the single shaft brain probe provides both recording and stimulating capability. A single shaft, rather than multiple shafts, minimizes the harmful effects of the surgical procedure. It is another object of this invention to provide a single multichannel brain probe that provides both recording and stimulating capabilities in a single device.

This device may be used in chronic (greater than one day) neuroscience applications to record electrical activity with amplifiers from live tissue by putting current or voltage through electrode wire contacts. The device may also be used in animal acute (less than one day) neuroscience applications for recording electrical activity with amplifiers from live tissue or stimulating live tissue by putting current or voltage through electrode wire contacts.

The device is most useful for recording and/or stimulation in human applications for targeting populations of neurons for various applications such as deep brain stimulation (DBS) procedures or other such procedures where multiple recording electrode sites and large stimulating electrode sites are required in acute human brain surgeries.

The manufacture of a multichannel microprobe is a difficult task and new engineering and manufacturing techniques are necessary to produce an extremely small yet effective device. Techniques such as the use of small electrically conducting wire and micro welding as well laser drilling of holes have been found to be useful. Additionally, different arrays of sites and combinations of electrodes are presented. It is another and further object of this invention to disclose new and useful manufacturing practices to provide a many new and novel brain probes with new and varied functions.

Other useful and innovative objects of this invention an disclosure will become obvious upon reading the below described Specification of this invention.

BRIEF DESCRIPTION OF THE DEVICE

A multichannel brain probe for intraoperative uses has an upper stainless steel section attached to a lower recording and/or stimulating section. Both the upper and the lower sections are cylindrical and both have an extremely small cross-section. The lower section comprises concentric cylindrical tubes and electrodes in specific applications. The outer cylindrical tube is an insulating tube and has holes drilled through it in desired patterns. Inside this tube is a second insulating tube. Recording/stimulating wires are positioned in the area between these two insulating tubes. One end of the wires protrudes out of the holes and the other end of the wires are threaded through the entire device and connected to an electronic interface. Other electrodes may also be present in certain applications of the brain probe. These could include an inner conductor electrode, covered by a cylindrical or tubular insulator. A tubular electrode, surrounding the inner conductor electrode and its insulating cover tube, may also be utilized in practicing this invention. The combination of electrodes and wires allows for precise mapping and/or stimulation of brain functions in a human or animal.

BRIEF DESCRIPTION OF THE DRAWINGS

FIG. 4 is the best view of the device.

FIG. 6 is a dimensional side view of the tip of the device and a detail view of one of the holes in the tip shaft of the device.

FIG. 7A is a detail cutaway view of one preferred pattern embodiment of the holes of the device. The actual holes are round but are shown as oval in some instances because they are cut into a rounded surface.

FIG. 7B is a detail cutaway view of an alternate dual pattern embodiment of the holes of the device.

FIG. 7C is a detail cutaway view of another alternate spiral pattern embodiment of the holes of the device.

FIG. 7D is a detail cutaway view of another alternate pattern embodiment of the holes of the device.

FIG. 14 is a side view of the device showing both the distal and proximate ends.

FIG. 15A is a side view of an alternate embodiment of the single shaft brain probe showing four shafts attached to a connector.

FIG. 15B is a side view of an alternate embodiment of the single shaft brain probe with flexible wires attaching the shaft to the connector.

FIG. 16 is a detail view of an ultra-small brain probe.

DETAILED DESCRIPTION OF THE PREFERRED EMBODIMENT

A multi-channel brain probe 1 offers an improvement over the prior art in that it allows many different electrical functions to be performed intraoperatively and otherwise. The new brain probe 1 has an extremely small cross-section and may be used in surgical and deployed operations.

Figure 1:
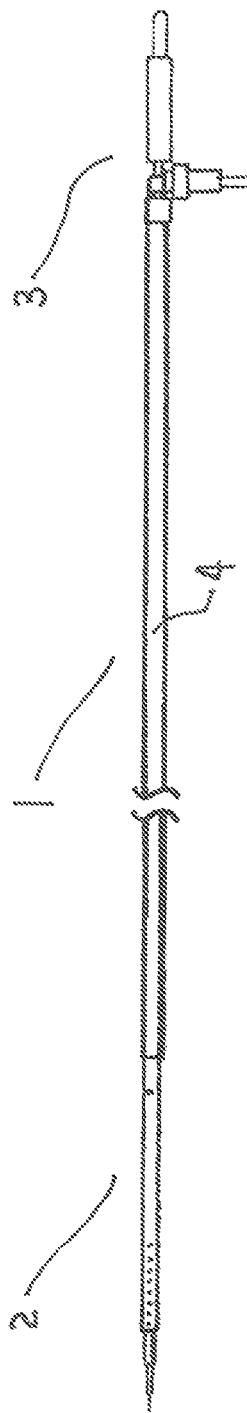
FIG. 1 is a side view of the brain probe.
Figure 3:
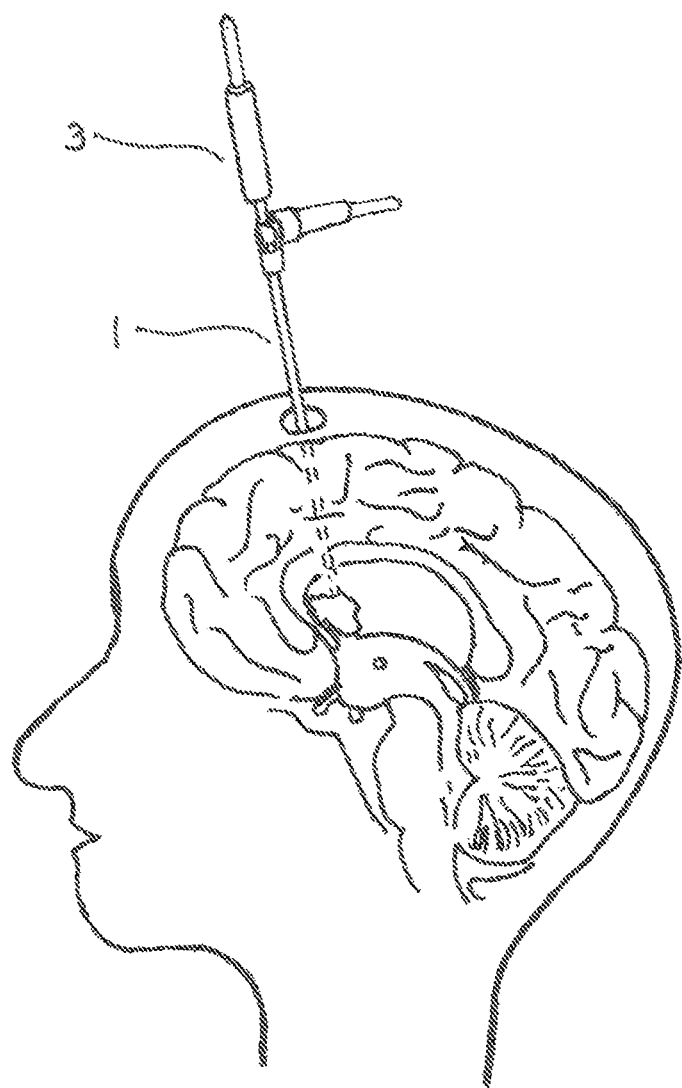
FIG. 3 is a pictorial view of the brain probe as it is to be inserted into the brain of a subject.
Figure 4:
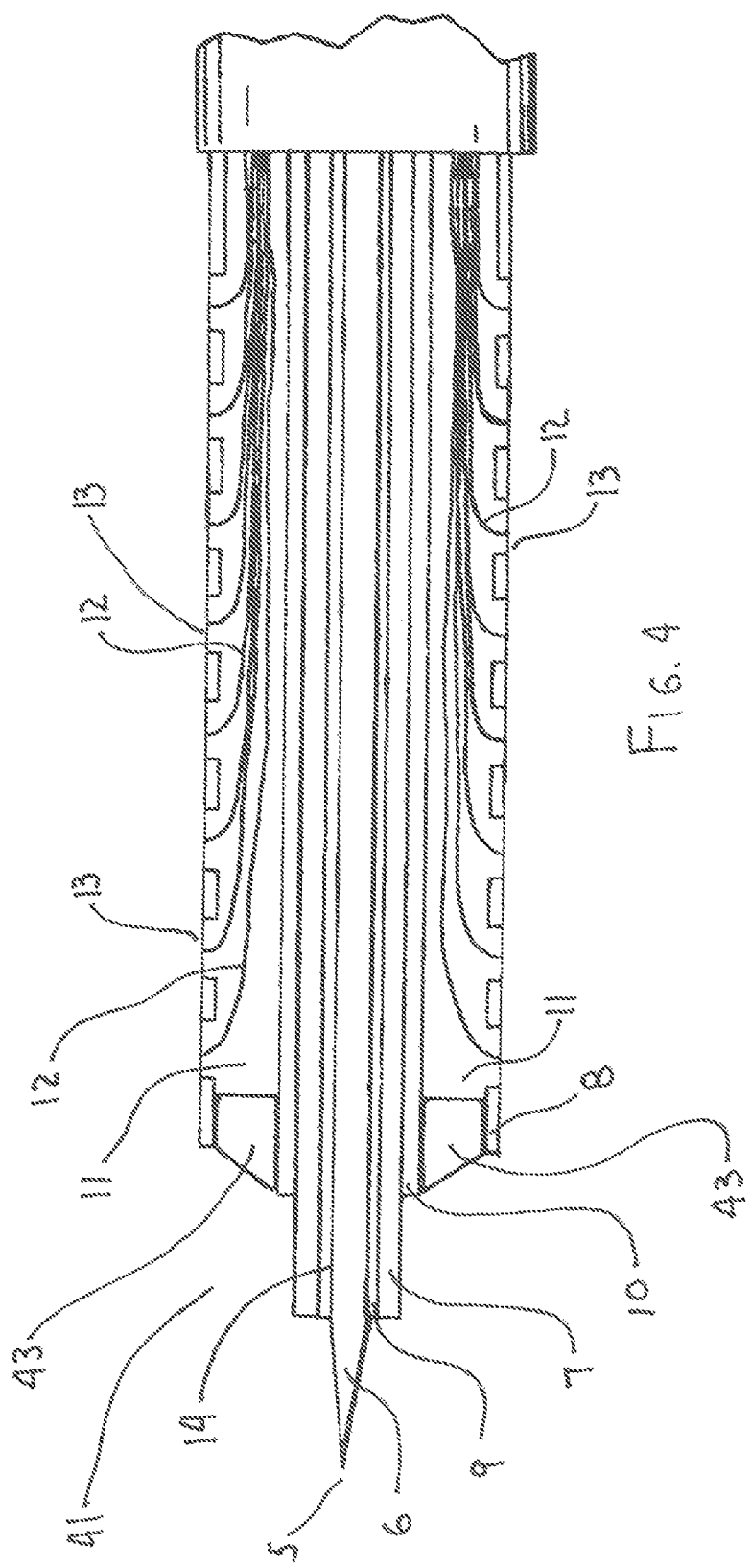
FIG. 4 is a detail view of the very tip of the brain probe.

As best shown in FIG. 1, the brain probe 1 has a distal end 2 and a proximal end 3. The distal end 1 may have one or more electrodes that contact the tissue of the subject while the proximal end connects to a computer or other recording, stimulating or multi-function electronics. The brain probe 1 has two main sections, an upper, tubular neutral stainless steel shaft or shank 4 and a lower distal end 2 section. The distal end section 2 comprises one or more electrodes, insulators and wires as will be explained. The very tip distal end 5 of the brain probe 1 is sharpened as shown in FIG. 4. The brain probe is inserted through the skull and into the meninges and brain matter as shown pictorially in FIG. 3.

Figure 2:
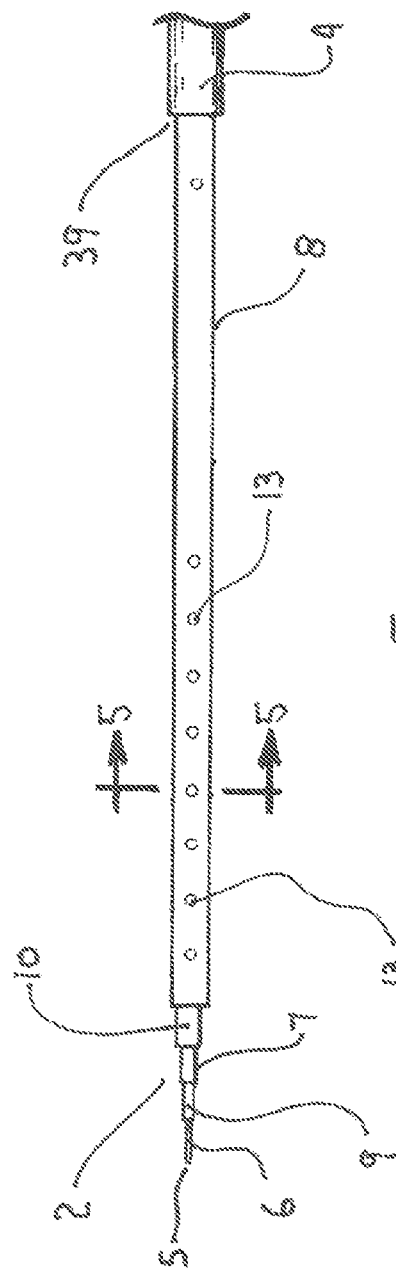
FIG. 2 is a detail side view of the tip of the brain probe.

Turning to FIG. 2, the major components of brain probe 1 are shown. These components, in the preferred embodiment, comprise an inner conductor electrode 6, a stimulating electrode 7 and an outer, lower cylindrical insulation tube or shaft 8. The upper 4 and lower 8 tubular shafts are connected together and are continuous after the manufacturing process. The lower shaft has one end continuous with the upper shaft. The other end is sharpened to a point. The main electrical components 6, 7 and 12 are separated by insulating materials.

The inner electrode 6 and stimulating electrode 7 are separated by an insulating tube 9 as shown in FIGS. 2 and 4. There is also an insulating tube 10 between stimulating electrode 7 and the outer insulation tube 8. Glue 11 separates and insulates outer insulation tube 8 and second insulation tube 10. This glue 11 also contains and surrounds the electrode stimulating and/or recording wires 12. The outer tube 8 has a plurality of electrode simulating and recording wire holes 13 as best shown on FIGS. 2 and 4.

Figure 5:
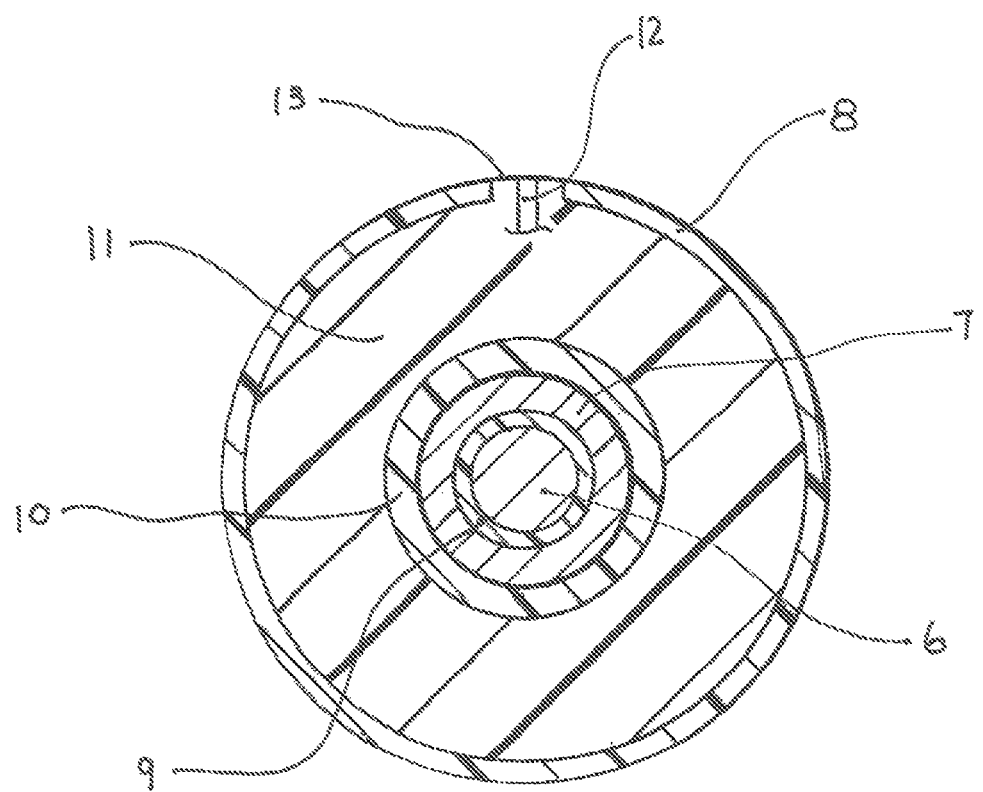
FIG. 5 is a cutaway view of the distal end of the device taken along Lines 5-5 as shown in FIG. 2.

FIGS. 4 and 5 show the configuration and relationship of the important parts of the distal end sensors and stimulating electrodes. Each sensor or electrode must be insulated from any other sensor or electrode. Sharpened inner electrode 6 is made of medical grade metal such as tungsten, platinum-iridium, pure iridium or stainless steel. Since this electrode will come into contact with a patient's brain tissue, it is important that the metal used is medical grade. Electrode 6 has an inner shaft diameter of 0.075 to 0.5 millimeters and is sharpened to a point and insulated with Parylene-C or other acceptable biocompatible non-conducting polymer.

The tip of electrode 6 has some of its insulation removed and is exposed so that the tip has an impedance between 0.005 and 2.5 megohm measured at 1.0 kilohertz. This electrode 6 can be used to record neural activity or it can be used to pass current into the tissue. Electrode 6 is connected to a dedicated external connector or, alternatively, it can be connected to a multicontact connector. Connectors will be described later in this Specification.

Inner conductor electrode 6 can also be an uninsulated sharpened metal conductor that can be used as either a reference ground or ground electrode in a different embodiment of the device. It is to be understood that all the dimensions and electrical values used here and in the remainder of this Specification are for purposes of illustration only and are not meant to be specific limitations. The brain probe 1 has many diverse uses and applications depending upon the specific applications for which it is being used. This second inner conductor electrode 6 is located inside and is concentric with the first inner tubular electrode 7.

The stimulation electrode 7 is a metal tube electrode typically made of stainless steel. Electrode 7 has a linear exposure of between 0.25 to 2.0 millimeters. Electrode 7 is connected to a dedicated external connector or it can be connected to a multi-contact connector as will be explained later. As in the description of electrode 6, stimulating electrode 7 is optional depending upon its specific use and application. First inner tubular conductor electrode 7 is located inside and concentric with lower outer tubular shaft 8.

A plurality of electrode recording or stimulating wires 12 are comprised of an outer insulating material and an actual inner metal wire. The inner electrical conductor can be made of platinum-iridium, pure iridium, tungsten, stainless steel or any biocompatible metal. The inner conductor is insulated with Polymide or any other non-conductive polymer. It has been found that at least 4 wires are preferred. The wires 12 are cut flush with the outer surface of tube 8 in the manufacturing process. This process and procedure will be explained later in this description but is shown graphically in FIGS. 8-12. A typical diameter of the wires 12 is between 12.5 and 50 microns (0.0125 to 0.050 millimeters). Multiple wires 12 are utilized in practicing this invention as shown in FIG. 4. Two or more wires 12 may also be bundled together to emerge from the same wire holes 13 located on the outer part of outer tube 8 to increase the surface area of the metal contact for recording or stimulation or for recording LFPs (low frequency potentials).

Stainless steel shaft 4 is hollow and is utilized to enable the surgeon to have a greater length of penetration, if desired, into the brain or other tissue. The shank 4 can also be used for ground or reference by electrically attaching it to an external dedicated connector or to a multi-connector. The diameter 17' of shank 4 is a function of the diameter of the outer insulation tube 8 since outer insulation tube 8 fits inside hollow shank tube or 4.

Insulation of the various electrical electrode and wires is critical to the proper functioning of the device.

The primary insulation 14 on the top surface of electrode 6 is a non-conductive polymer or other biocompatible material such as Parylene-C or PTFE Teflon. This insulation on electrode 6 can be exposed at the sharpened tip 5 to expose the metal underneath to have a specified impedance value.

The insulation 9 between inner electrode 6 and stimulation electrode 7 is typically Polymide or another biocompatible material such as PTFE Teflon. The inner diameter of tube 8 must be able to fit over inner electrode 6 at a minimum.

Insulation 10 between inner stimulation electrode 7 and electrode stimulation/recording wires 12 is also typically Polymide or another biocompatible insulating material such as PTFE Teflon. The inner diameter of the inner tube 8 is also required to fit over both electrode 6 and stimulating electrode 7 if both electrodes are being used in a particular manufacturing application.

The insulation over the electrode wires 12 is typically Polymide or any other biocompatible insulating materials. Other biocompatible insulating materials are well known in the art and are claimed as part of the new, novel and unique brain probe described herein.

The insulation tube 8 in typically Polymide or other biocompatible insulating material such as PTFE Teflon or PEEK. The inner diameter of insulating tube 8 is a function of the number of wires 12 and wire holes 13 used in the manufacture of a particular brain probe. The inner diameter of tube 8 is also affected by which combination of inner electrode 6, stimulation electrode 7, and insulators 9, 10 and 14 are utilized in a particular brain probe manufacture and application.

The particular glues utilized are also important to the manufacture, use and performance of this device. A medical grade cyanoacrylic or very low viscosity medical grade epoxy is used for bonding inner electrode 6 to insulation tube 9 and for bonding insulation tube 9 to stimulation electrode 7.

Figure 9:
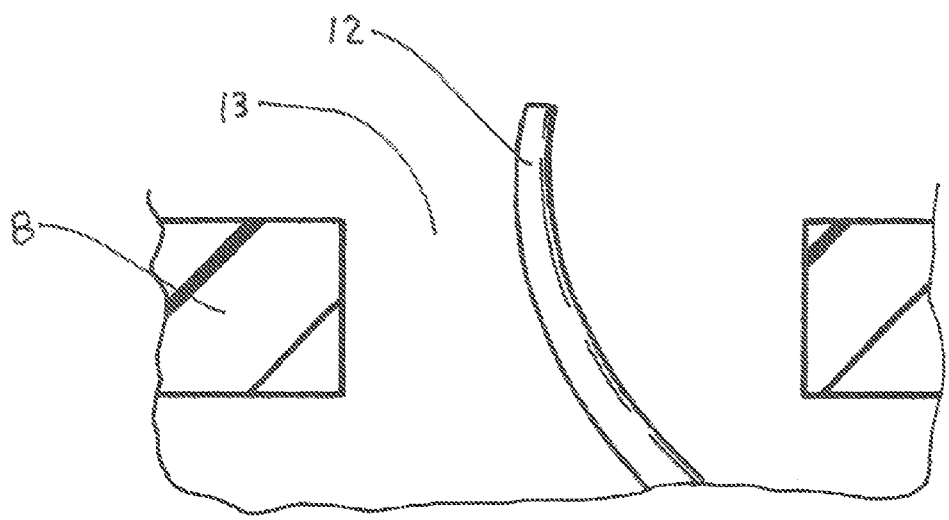
FIG. 9 is a detail cutaway view of the distal end of the device showing one hole of the device showing the initial placement of the wire.
Figure 11:
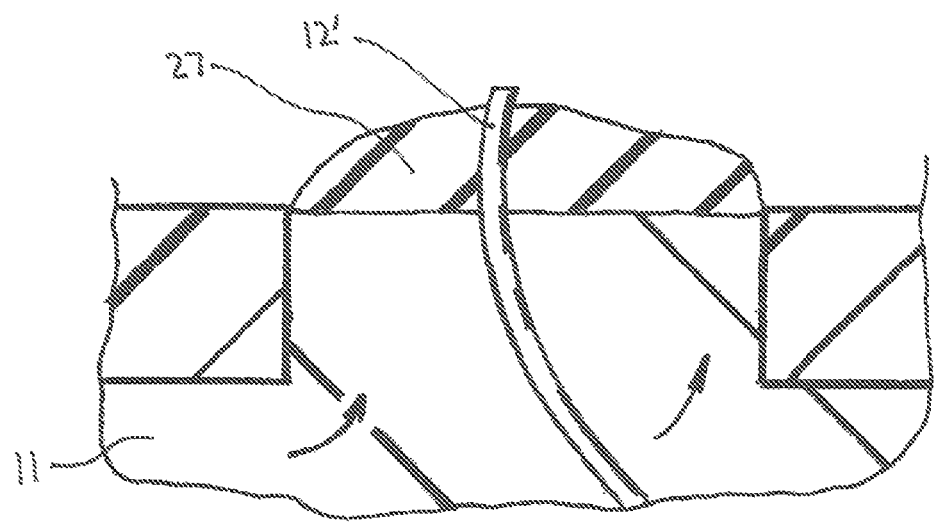
FIG. 11 is a detail cutaway view of one hole of the device showing the application of the epoxy to the inside of the device.

Glue 11 is of particular importance in practicing this invention. Glue 11 is used in between insulating tube 10 and the outer insulation tube 8. This glue is used to fill the void between 8 and 10 once wires 12 have been inserted into the void and properly aligned in holes 13. Inserted wires 12 before the injection of the glue are shown in FIG. 9. Once wires 12 have been inserted into the void between 10 and 8 this glue 11 is injected into the void and fills the area between 10 and 8 completely, up to the outer surface of tube 8. Silicone 27 is then applied above hole 13 on the top surface of tube 8 as best shown in FIG. 11. The wire 12 protrudes out through the hole 13 but remains sealed in silicone 27 as shown. As shown in FIG. 11, the excess silicone is then removed from the outside of tube 8 by either mechanically peeling or dissolving, or both, the silicone 27. Precision wire cutters or other process are then used to cut wire 12 flush to the outer surface of tube 8.

Figure 8:
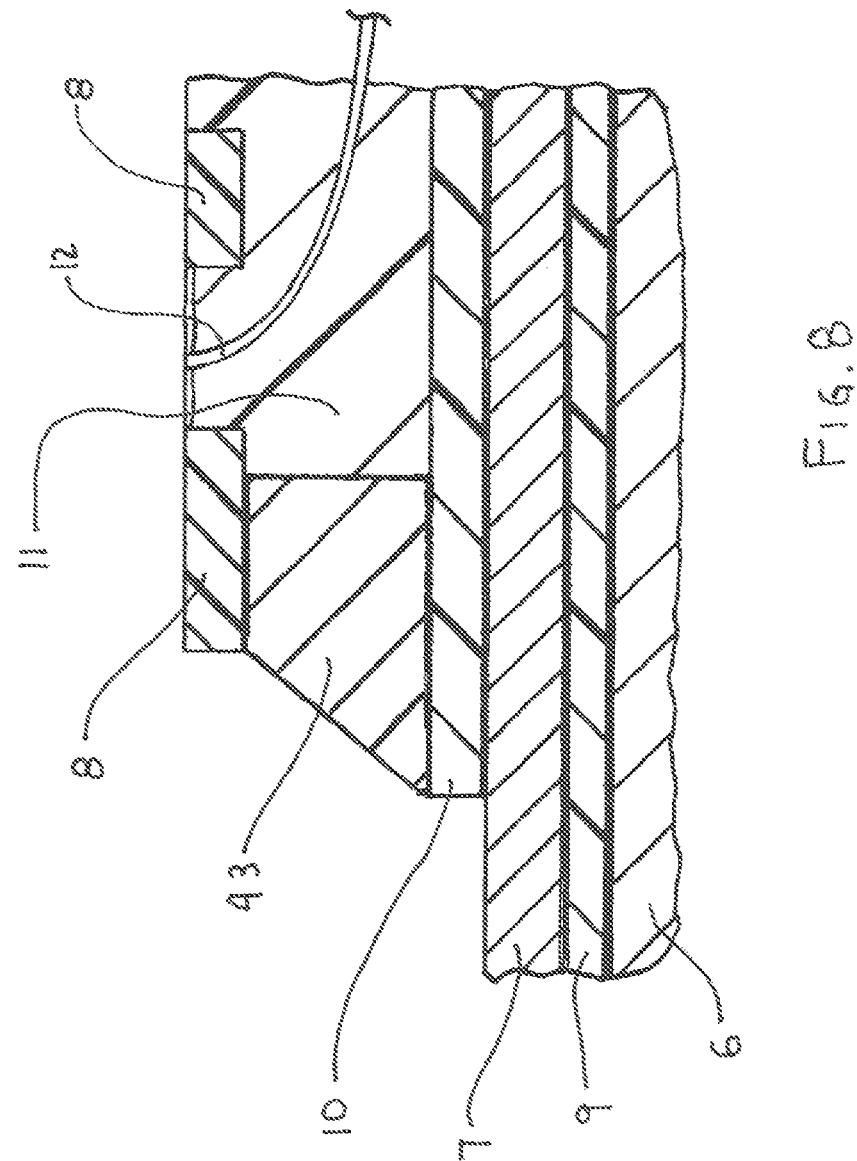
FIG. 8 is a detail cutaway view of the distal end of the device showing one hole with the wire in place and sealed with epoxy.
Figure 8A:
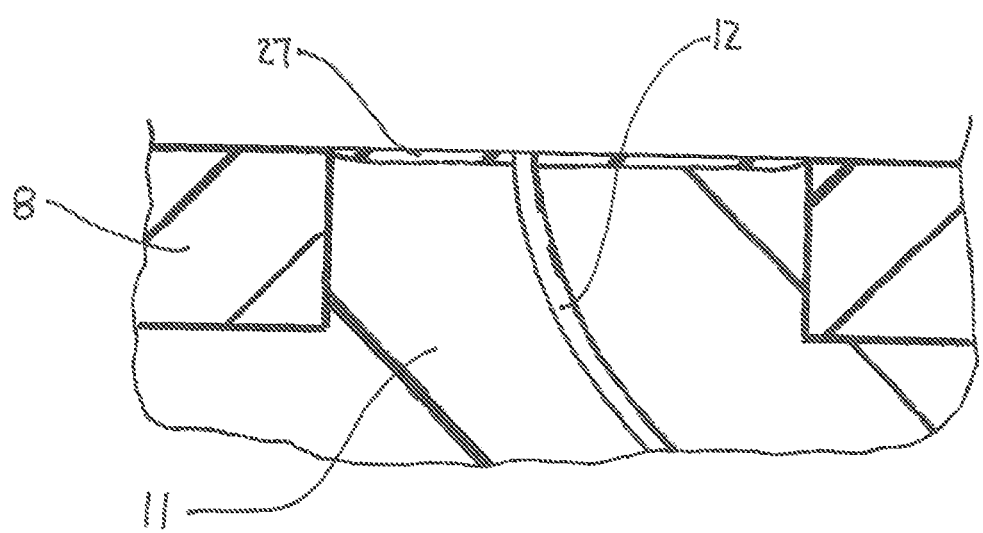
FIG. 8A is a detail of the hole shown in FIG. 8.

Finished site 13, as best shown in FIGS. 8 and 8A comprises the electrode wire or wires flush with the outer surface of outer insulation tube 8. The metal surface of the inner metal wire comes into contact with the tissue of the patient for recording or stimulation purposes.

Outer insulating tube 8 is also glues to the stainless steel shank 4 with medical grade cyanoacrylate or very low viscosity medical epoxy.

Turning now to FIG. 6, the dimensions of the preferred embodiment are shown. It is to be understood that the dimensions shown and described are of a preferred embodiment and are not a limitation on the brain probe device. Many variations of the multichannel brain probe are within the disclosure and contemplation of this device. For example, inclusion of an inner electrode conductor 6 is optional as is the inclusion of the stimulation electrode 7. Additionally, the number of wires 12 may also vary and the placement, configuration and number of wire holes 13 may also vary. The following dimensions are typical, however, and describe the general size of the components.

The size of the holes 13 and the distance 22 between holes 13 are a function of the size of the wire or bundled wires designed to be threaded through the hole 13. In the preferred embodiment, the hole diameter 16 is proportional to the number and size wire going through hole 13. Holes 13 are generally spaced 0.050 to 1.0 mm apart. The most distal hole is typically 0.5 to 1.0 mm from the tip of insulation tubing 8 as shown by dimension 20 on FIG. 6.

The general length 17 of the stainless or microfill tube 4 can vary from 5 to 310 mm while the overall length of the polymide insulation tube 8 varies depending on the specific application for which it is intended. The diameter 17' of the stainless steel shaft is a function of the diameter of the distal end components that must fit inside the shaft 4. The maximum length 18 of polymide tube may vary from between 5 to 50 mm. These lengths may vary depending upon the specific application for which the probe is intended. Dimensions given here are for purposes of illustration only.

In the preferred embodiment, the length 19 from the distal tip end of polymide insulation tubing 8 to the distal tip end of tungsten electrode 6 will vary depending on the specific application. The diameter 21 of insulation tubing 8 is a function of whether or not the embodiment includes electrodes 6 and 7 and the size and number of wires 12.

Recording sites may vary and may be designated as "n" recording sites for purposes of this invention. Recording sites n coincide with the holes 13. The distance between holes 13 (and hence recording or stimulation sites n) is approximately 0.1 to 1.0 mm in the preferred embodiment but may vary independently depending upon the number of recording sites needed in any variation of the device. An exact number of holes or their placement is not a limitation on this invention as many different numbers and placements of recording sites is well within the spirit and disclosure of this invention.

The placement and configuration of electrode wires 12 (and thus recording sites n) are best shown in FIGS. 7A, 7B, 7C and 7D. The instant invention contemplates the placement of between 4 and 128 wires in outer insulation tube 8 in a variety of arrays. Holes 13 (recording sites n) depends upon the design and actual use of the brain probe 1. Holes can be placed anywhere along insulating tube 8 as well as circumferentially and in groups. The holes 13 are finished using mechanical or laser drilling. Laser drilling is more precise.

Examples of arrays are found in drawing FIGS. 7A-7D. Recording sites n may be located in a linear distribution 23 on one side as shown in FIG. 7A. They may be located in a linear distribution on opposite sides 24 as in FIG. 7B. They may be located in a spiral distribution 25 as shown in FIG. 7C. They may also be placed in groups of 2, 3 or 4. Distribution in groups 26 of 4 is shown in FIG. 7D and can provide multiple tetrode groupings.

Electrode wires 12, comprising an outer wire insulation and inner metal conductor are typically pre-insulated with Polymide or some other non-conductive polymer. In manufacture, the wires are cut 20 percent longer than the total length of the LMA brain probe 1. The wires 12 are then threaded through the hole 13 of insulating tube 8 and pushed up and out the insulation tube 8. At the hole 13 of the tube 8, the hole end of each wire 12 extends out of the hole 13 and past the outer surface of tube 8 by approximately 1 cm. The connector end of each wire is attached to a multi-contact connector 28 by soldering or microwelding. In this process, it is important to note and detail which hole 13 and wire 12 is attached to which connector position.

A plurality of wires 12 is located inside the outer tubular shaft 8. As many wires 12 as are needed in each embodiment are threaded through the outer insulation tube 8 between tube 8 and insulation tube 10. Each wire 12 has a hole end of each wire protruding out of a hole 13. The connector end of each wire is soldered or micro welded to a particular contact on the connector 28. This process is repeated for as many wires as are needed in the particular embodiment until all holes 13 have been populated.

After all wires 12 have been threaded through all holes 13 forceps or other tools are used to insure that the wire 12 extends past the outer surface of tube 8 as best shown in FIGS. 9-12. A thin coat of silicone 27 is then applied over each hole 13 to insure that epoxy 11 does not extend beyond the outer surface of the hole 13 when the epoxy 11 is injected to fill the space between tubes 8 and 10.

In embodiments wherein a hole position will be used to record single neuron action potentials, low frequency potentials (LFPs), or to stimulate with electrical current, a single hole can be made larger in order to accommodate a bundle (more than one) of wires. Bundling multiple wires together increases the surface area of the wire ends. In this case, the connector ends of all wires bundled together will be connected to the same contact on connector 28. Wires going through the same hole and bundled together are then by definition electrically parallel. Multiple wires through holes 13 may be attached to different contacts for other applications.

Figure 10:
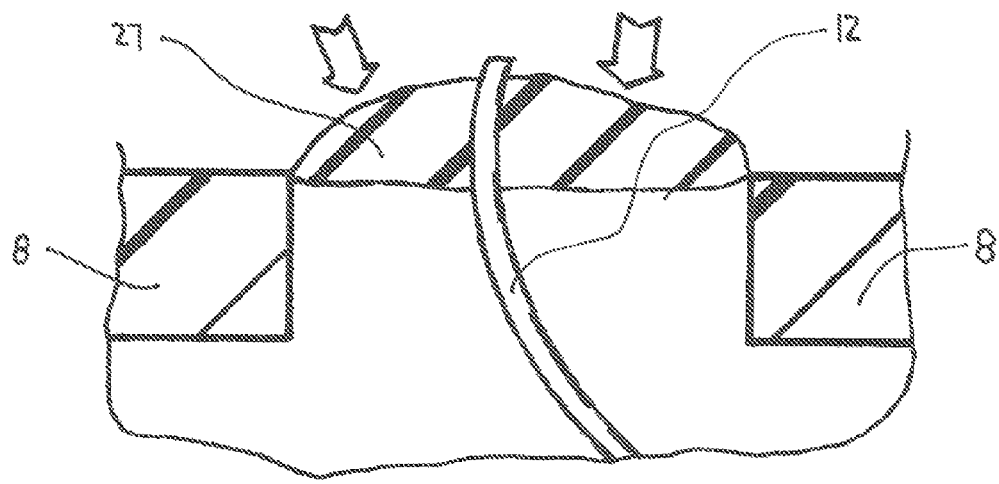
FIG. 10 is a detail cutaway view of the device showing the silicone as applied to top of the hole and the wire.
Figure 12:
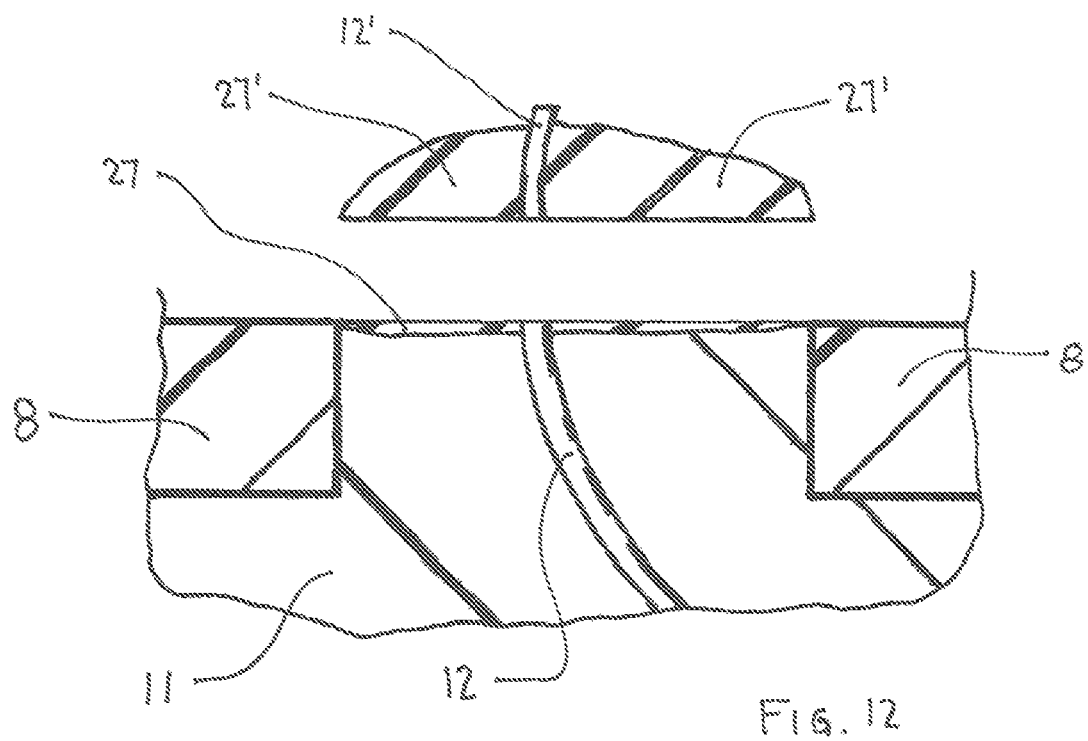
FIG. 12 is a detail cutaway view of the finished wire installation showing the removal of the excess wire and silicone.

FIGS. 9 through 12 illustrate the method of manufacture of a preferred embodiment of this brain probe. FIG. 9 shows the wire comprising the wire insulation 15 and the inner metal conductor as it is being pulled upward and outward through hole 13. A layer of silicone 27 is then placed on top of hole 13 as shown in FIG. 10. Epoxy 11 or other suitable insulating material is then forced into the area between insulation tube 8 and tube 10 such that the epoxy goes up to the upper surface of hole 13 and stops where the silicone 27 has been applied over hole 13 and emerging wire 12 as shown in FIG. 11. The top end 12' of wire 12 and the top end 27' of silicone 27 is then finished by cutting off the top flush with the top outer surface of tube 8 as shown in FIG. 12. The silicone 27 and excess wire are discarded. The inner conductor wire is left exposed as shown in FIG. 12. The inner top metal surface of conductor wire 12 is able to contact the tissue of the subject when the probe is inserted. The finished product along with the other elements of the brain probe is shown in FIGS. 8 and 8A.

Figure 13C:
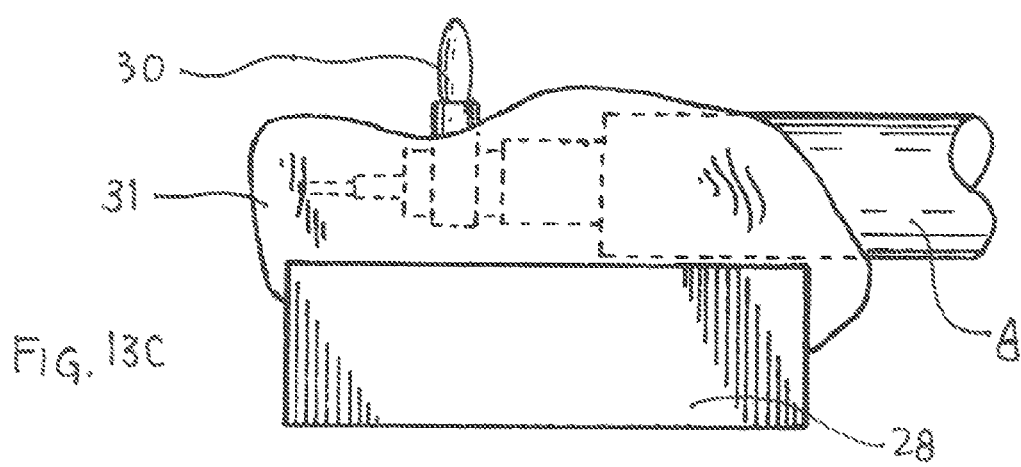
FIG. 13C is a schematic view of another alternate embodiment of the proximal end of the device showing an alternate connecting mechanism.
Figure 13B:
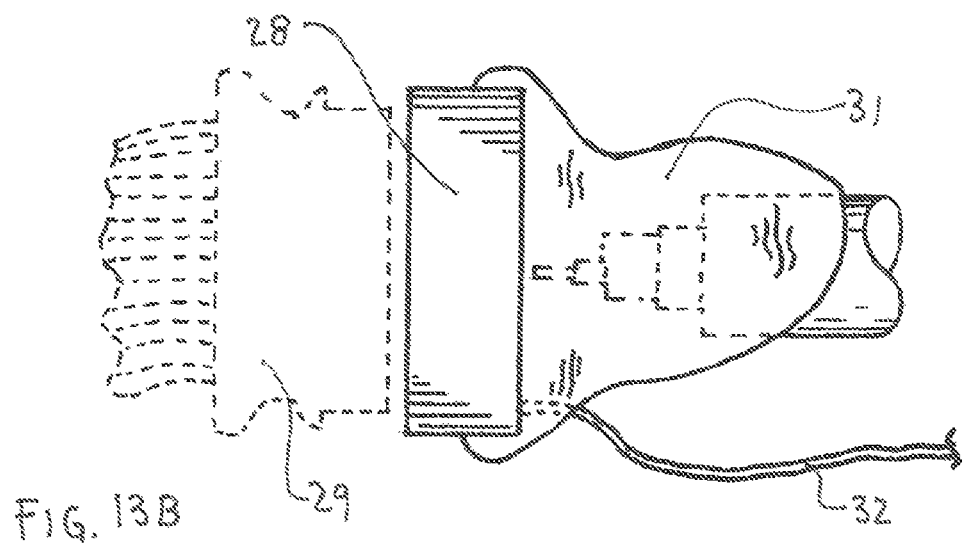
FIG. 13B is a schematic view of an alternate embodiment of the proximal end of the device showing the connector in another orientation.
Figure 13A:
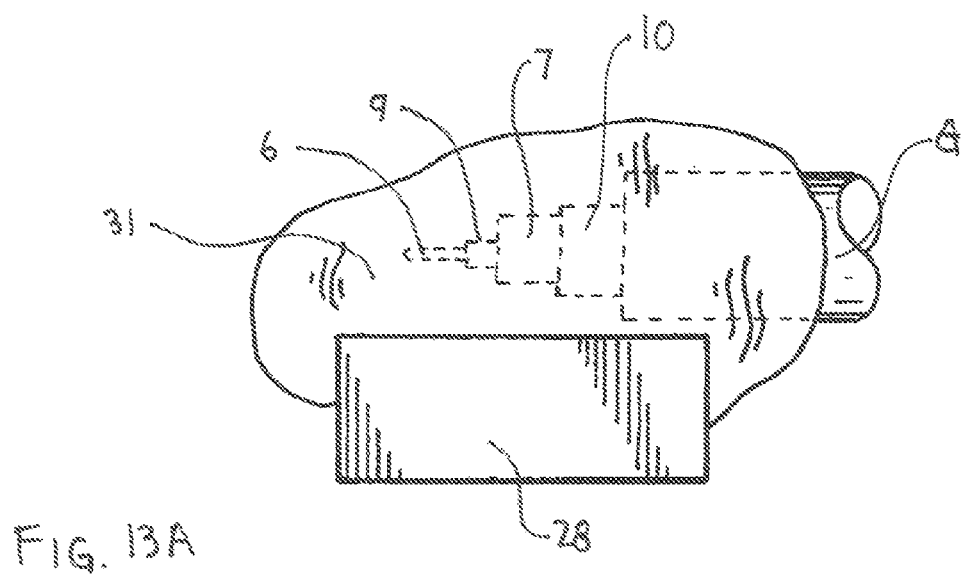
FIG. 13A is a schematic view of the preferred embodiment of the proximal end of the device showing the connector.

The wires 12 are then threaded through both the lower 8 and the upper 4 shafts. The other connector ends of inner electrical conductive wires 12 are soldered to contacts on electrical connector 28. Connector 28 is a standard connector well known and utilized in this industry. Connectors 28 are well known in the art and are manufactured by, for example, Omnetics Connector Corporation and Samtec Corporation. These connectors are shown on FIG. 13. The connector wire ends are soldered to contacts on connector 28. The outer interface of connector 28 is then electrically connected to a mating connector 29 that will interface to an amplifier, stimulator, data acquisition or a computer interface. The connector 28 is basically a multichannel connector device that connects through a mating connector to an amplifier, stimulator, data acquisition or computer to the wires 12 or other electrodes. The inner part of the connector and the wires electrically connected to the connector 28 are then covered with epoxy 31 as shown in FIGS. 13A, 13B and 13C. Different orientations of the multi contact connectors as shown in FIGS. 13A and 13B is within the spirit and disclosure of this invention.

FIG. 13B shows an optional ground reference wire 32 from the multicontact connector 28 that protrudes out of the epoxy 31.

FIG. 13C shows an alternate connector with a pin 30 protruding through the epoxy. Pin connector 30 would usually be electrically connected to stimulating electrode 7.

FIG. 14 is a side cutaway view of the inner conductor electrode 6 and the stimulating electrode 7 in the assembled and preferred embodiment of the brain probe 1.

Inner electrode 6 can be made of tungsten or other suitable metal and have a length of up to 310 mm. The typical diameter of electrode 6 is from 0.075 to 0.50 mm. If the electrode 6 is used for recording electrical activity or for stimulating with electrical current it is insulated 9 with Parylene or another suitable polymer or epoxy compound. Electrode 6 is sharpened at its distal end 41 to a specified tip diameter. The tip diameter is a function of the desired electrical properties of the electrode. The electrode 6 tip is exposed using high voltage plasma or a laser to have a surface area required for either recording or stimulating. The amount of exposure is a function of the uses for the electrode in a particular application.

Inner electrode 6 is covered, or surrounded, by insulation. This insulation usually takes the form of a polymide or other suitable polymer tube insulating tube 9 as previously described. The inner diameter of insulating tube 9 is such that it fits tightly over the inner electrode 6. This insulating tube 9 is glued at a specified and designated distance from the distal end 41 of electrode 6. Insulating tube 9 extends nearly the entire length of electrode 6 leaving only 2 to 10 mm without Polymide tubing insulation at the proximal end 40 of electrode 6.

Stimulating electrode 7 is made of stainless steel or another biocompatible metal. Stimulating electrode 7 has an inner diameter such that it fits tightly over Polymide insulating tube 9. Stimulating electrode 7 is polished at the distal end 41 and is glued to insulating tube 9. Stimulating electrode 7 is shorter than electrode 6. Insulation tube 10 has an inner diameter that such that tube 10 fits tightly over stimulating electrode 7 as shown in FIG. 14. Insulating tube 10 is glued to stimulating electrode 7 leaving approximately 0.25 to 2.0 mm exposed at the distal end 41. Insulation tube 10 extends to within approximately 5 mm of the proximal end 40 of the inner electrode 6. The proximal end of the electrodes 6 and 7 and staggered so that no electrical connections can be made between the two electrodes as is standard in this art.

The integration of electrodes 6 and 7 and threaded electrode wires 12 within outer insulating tube 10 is done in the following manner. One first assures that the proximal ends 40 of electrodes 6 and 7 as shown in FIG. 14 do not have any sharp edges. Manufacturing assembly 6, 7 and 9 (inner electrode 6, insulation tube 9 and stimulating electrode 7) is inserted into outer insulating tube 10 after the threaded wires 12 have been inserted into holes 13 and threaded through the area between insulation tube 10 and outer insulation tube 8. Assembly comprising 6, 7 and 9 is twisted as it is being pushed into tube 10 to minimize the force necessary.

After manufacturing assembly A has been inserted approximately 80 to 95 percent of the required distance through outer tube 8, epoxy glue 11 is injected into the area between tubes 10 and 8 as shown in FIGS. 8-12 and previously described until the epoxy 11 begins to emerge out the proximal end 40 of tube 8 the assembly. The manufacturing assembly A is then inserted further into tube 8 to the specified distance insuring that the assembly A is centered within tube 8.

Assembly A must be centered within and concentric with outer tube 8 perfectly. To insure the perfect eccentric alignment of assembly A and tube 8 a stainless steel or Polyimide collar 43 is inserted between tube 8 and tube 10 at the distal 41 of the device as best shown on FIG. 4.

The epoxy in the assembled unit is then cured in an oven at a specified temperature.

Silicon is then removed from the outer surface of the outer tube 8. Special scissors are then used to cut the metal wires 12 so that they are flush with the outer surface of outer tube 8. The technician then slides stainless steel tube 4 over the entire assembly if it is required to extend the length of the brain probe. Stainless steel tube 4 is then glued in place using an appropriate biocompatible glue.

In practicing this invention, different presentations of the brain probe 1 are well within the contemplation of this disclosure. For example, as shown on FIG. 15A a plurality of probes 34 may be connected to a single connector 33 or to multiple connectors. This type of multi-shank LMA design is ideal for acute or chronic applications. However, each shank can have up to 64 electrode sites, and therefore multiple connectors may be required for this type of deployment.

Another type of brain probe can have tethered probes 35 using flexible electrically conductive cables 36 and 37. Conductive cables contain the wires 12 that are encased in silicone adhesive and/or a silicone tube. This brain probe with flexible output cables 36 and 37 has been designed specifically for chronic applications. The fine leads 36 and 37 are coiled together and coated with a silicon elastomer, allowing the shank 35 to virtually float in the brain tissue without harming the subject.

Also within the disclosure and contemplation of this invention is an ultra-small brain probe 38 with flexible cables.

It is to be understood that many different variations of the instant device are within the spirit and contemplation of this invention. Different size primary electrodes 6 and 7 can be manufactured to different electrical specifications by varying the diameters or surface tip exposure of the electrodes. Additionally, many different patterns of holes or number and size of electrode wires 12 are contemplated. Dimensions given are for purposes of illustration only and are not meant to be limitations on the scope of the disclosure.

Having fully described my new invention, I claim:

1. A multichannel brain probe for insertion into the brain of an animal or human for recording and/or stimulating a subject, comprising:
   (a) a smooth tubular outer insulating shaft having an upper end and a lower end wherein the lower end of said shaft has a sharpened point and wherein said tubular shaft has a plurality of electrode stimulating and recording holes in its outer surface wherein said holes can be placed anywhere along said tubular shaft;
   (b) a plurality of flexible conducting wires located inside said tubular outer shaft wherein each conducting wire comprises an outer insulating material and an inner conducting wire each wire having one end located in one of said holes and the other end connected to an electrical connector interface;
   (c) an outer electrical connector interface located at the upper end of said tubular outer shaft electrically connected to one end of said wires; and
   (d) a medical grade insulating material glue inside the outer tubular shaft, said insulating material glue filling the area inside said outer insulating tube and supporting the wires.

2. A multichannel brain probe for recording and/or stimulating a subject as in claim 1 wherein the tubular outer shaft has at least 4 holes therein and comprising at least 4 wires.

3. A multichannel brain probe for recording and/or stimulating a subject as in claim 1, further comprising a first inner tubular conductor electrode inside and concentric with said tubular outer shaft.

4. A multichannel brain probe for recording and/or stimulating a subject as in claim 3, further comprising a second inner stimulating electrode located outside and concentric with said first inner tubular conductor electrode wherein said first and second tubular electrodes are separated by a concentric insulating tube.

5. A multichannel brain probe for insertion into the brain of an animal or human for recording and/or stimulating a subject as in claim 1, wherein said medical grade insulating material glue is medical grade epoxy.

6. A multichannel brain probe for insertion into the brain of an animal or human for recording and/or stimulating a subject as in claim 1, wherein two or more of said conducting wires may be bundled together to be inserted into enlarged holes.

7. A set of multichannel brain probes for insertion into the brain of an animal or human for recording a subject, comprising two or more individual brain probes electrically connected to each other comprising:
   (a) two or more multichannel brain probes, each brain probe comprising:
      (1) a tubular outer insulating shaft having an upper end and a lower end wherein the lower end of said shaft has a sharpened point wherein each tubular shaft has a plurality of electrode stimulating and recording holes in its outer surface wherein said holes can be placed anywhere along said tubular shaft;
      (2) a plurality of flexible conducting wires located inside said outer tubular shaft wherein each conducting wire comprises an outer insulating material and an inner conducting wire, each wire having one end located in one of said holes and the other end connected to an electrical connector interface;
      (3) an electrical connector interface located at the upper end of said tubular shaft electrically connected to one end of said wires;
      (4) a medical grade insulating material glue inside the outer tubular shaft, said insulating glue filling the area inside said outer insulating tube and supporting the wires; and
   (b) a mating electrical connector electrically connected to each electrical connector interface of each of said two or more brain probes.

8. A set of multichannel brain probes for insertion into the brain of an animal or human for recording a subject as in claim 7, further comprising a plurality of flexible electrically conductive tether wires, each flexible tether wire having one end connected to the outer electrical connector interface and the other end connected to the mating electrical connector.

* * * * *